US008338348B2

(12) United States Patent
Anim-Danso et al.

(10) Patent No.: US 8,338,348 B2
(45) Date of Patent: Dec. 25, 2012

(54) SKIN CLEANSING COMPOSITIONS WITH POLYGLYCEROL ESTERS AND HYDROPHOBICALLY MODIFIED POLYMERS

(75) Inventors: Emmanuel Anim-Danso, Cuyahoga Falls, OH (US); Lisa Gandolfi, Franklin Park, NJ (US); Euen Thomas Gunn, Trenton, NJ (US); Russel M. Walters, Philadelphia, PA (US); Michael J. Fevola, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 12/974,188

(22) Filed: Dec. 21, 2010

(65) Prior Publication Data
US 2012/0157366 A1 Jun. 21, 2012

(51) Int. Cl.
*A61Q 5/00* (2006.01)

(52) U.S. Cl. ........ 510/130; 510/136; 510/138; 510/424; 510/475; 510/490; 510/505; 424/70.11

(58) Field of Classification Search ........................ None
See application file for complete search history.

(56) References Cited

U.S. PATENT DOCUMENTS

| | | | |
|---|---|---|---|
| 3,950,260 A | 4/1976 | Eldib | |
| 4,110,263 A | 8/1978 | Linderman et al. | |
| 4,186,113 A | 1/1980 | Verdicchio et al. | |
| 4,215,064 A | 7/1980 | Lindermann et al. | |
| 4,233,192 A | 11/1980 | Lindermann et al. | |
| 4,372,869 A | 2/1983 | Lindermann et al. | |
| 4,380,637 A | 4/1983 | Lindermann et al. | |
| 4,382,036 A | 5/1983 | Lindermann et al. | |
| 4,443,362 A | 4/1984 | Guth et al. | |
| 4,617,414 A | 10/1986 | Lukenbach et al. | |
| 4,726,915 A | 2/1988 | Verdicchio et al. | |
| 5,130,056 A | 7/1992 | Jakobson et al. | |
| 5,215,976 A | 6/1993 | Fost et al. | |
| 5,286,719 A | 2/1994 | Fost et al. | |
| 5,478,490 A | 12/1995 | Russo et al. | |
| 5,648,348 A | 7/1997 | Fost et al. | |
| 5,650,402 A | 7/1997 | Fost et al. | |
| 5,951,991 A * | 9/1999 | Wagner et al. | 424/401 |
| 6,468,614 B1 | 10/2002 | LeVine et al. | |
| 6,703,427 B2 | 3/2004 | Schmucker-Castner et al. | |
| 6,762,159 B2 | 7/2004 | Ishitobi et al. | |
| 6,897,253 B2 | 5/2005 | Schmucker-Castner et al. | |
| 7,157,414 B2 | 1/2007 | LiBrizzi et al. | |
| 7,335,627 B1 | 2/2008 | O'Lenick et al. | |
| 7,375,064 B1 | 5/2008 | O'Lenick et al. | |
| 7,507,399 B1 | 3/2009 | O'Lenick et al. | |
| 7,547,434 B2 | 6/2009 | Tierney et al. | |
| 7,754,666 B2 | 7/2010 | Walters et al. | |
| 7,803,403 B2 | 9/2010 | Librizzi et al. | |
| 2002/0031532 A1 * | 3/2002 | Uchiyama | 424/401 |
| 2005/0070452 A1 | 3/2005 | Librizzi et al. | |
| 2006/0018861 A1 * | 1/2006 | Chen et al. | 424/70.14 |
| 2006/0083703 A1 * | 4/2006 | Torgerson | 424/70.11 |
| 2006/0257348 A1 | 11/2006 | Walters et al. | |
| 2007/0111910 A1 | 5/2007 | Walters et al. | |
| 2008/0112913 A1 | 5/2008 | Librizzi et al. | |
| 2008/0113895 A1 | 5/2008 | Tamareselvy et al. | |
| 2009/0053337 A1 | 2/2009 | Hansenne et al. | |
| 2010/0129303 A1 * | 5/2010 | Dueva-Koganov et al. | 424/60 |

FOREIGN PATENT DOCUMENTS

| | | |
|---|---|---|
| DE | 198 18 410 A1 | 10/1999 |
| DE | 10 2008 059445 A1 | 6/2010 |
| EP | 1 559 774 A1 | 8/2005 |
| WO | WO 99/21530 A1 | 5/1999 |
| WO | WO2008060997 | 5/2008 |
| WO | WO 2009/016375 A2 | 5/2009 |

OTHER PUBLICATIONS

Fevola, M.J. et al., "A New Approach to Formulating Mild Cleansers: Hydrophobically-Modified Polymers for Irritation Mitigation", American Chemical Society, (2010) pp. 221-242.
Zana, Raoul, "Dynamics of Surfactant Self-Assemblies Miscelles, Microemulsions, Vesicles, and Lyotropic Phase", vol. 125 (2005) pp. 77-160.
European Communication dated May 31, 2012 from Application No. 11194698 EP Search Report.

* cited by examiner

*Primary Examiner* — Necholus Ogden, Jr.

(57) ABSTRACT

The methods and compositions of this invention relate to compositions containing polyglyceryl esters of fatty acids, low molecular weight hydrophobically-modified polymers and anionic and/or amphoteric surfactants having low irritation characteristics in combination with one or more additional characteristics, for example, relatively high clarity, relatively high foaming, and/or combinations thereof, as well as methods of making and using such compositions. These compositions have low pH values and are useful in cleansing the skin.

14 Claims, 2 Drawing Sheets

Figure 1. Difference in TEP test $EC_{90}$ of formulations compared to placebo.

SKIN CLEANSING COMPOSITIONS WITH POLYGLYCEROL ESTERS AND HYDROPHOBICALLY MODIFIED POLYMERS

FIELD OF THE INVENTION

The methods and compositions of this invention relate to compositions that exhibit low irritation characteristics in combination with relatively high foaming capabilities, as well as methods of making and using such compositions. These compositions are useful in cleansing the skin and other body parts including hair.

BACKGROUND OF THE INVENTION

Synthetic surfactant detergents, such as cationic, anionic, amphoteric, and non-ionic surfactants, are used widely in a variety of detergent and cleansing compositions to impart cleansing properties thereto. In addition, in certain compositions such as personal care compositions including shampoos and washes, it may be desirable to use combinations and levels of surfactants sufficient to achieve relatively high levels of foam volume and/or foam stability.

However, synthetic detergents tend to be irritating to the skin and eyes. As concentrations of such detergents in personal care compositions increase, so as to impart increased cleansing and foaming properties to these compositions, the irritation associated with such compositions also tends to increase, making such compositions undesirable for use on or near the skin and/or eyes.

Certain attempts to produce milder cleansing compositions have included combining relatively low amounts of anionic surfactants (which tend to be relatively high-foaming but also relatively highly irritating) with relatively lower irritating surfactants such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Unfortunately, mild cleansing compositions produced via both of such methods tend to suffer from relatively poor foaming and cleansing performance.

Furthermore, in connection with certain uses, consumers desire cleansing compositions to be relatively clear. In particular, clear compositions are often used advantageously to provide an aesthetic indication of purity to the consumer. However, a number of ingredients commonly used in conventional personal care compositions, including, for example, polymeric thickeners, tend to cause the compositions to become cloudy or opaque. It is not readily predictable which combinations of polymers, surfactants and other optional ingredients may be combined to create compositions that are suitable for use as cleansers and also exhibit high clarity.

U.S. Pat. No. 6,897,253 ('253) describes a substantially crosslinked alkali-swellable acrylate copolymer rheology modifier, water, an alkaline material, and an effective amount of surfactant so that a substantially insoluble compound is stabilized or suspended. Such polymeric rheology modifiers require a pH of 5 or 6 in order to build substantial viscosity. The addition of a hydrophobically modifies polymer ("hmp") to a surfactant system has been shown to result in a milder surfactant that still retains foaming performance (LiBrizzi et al., U.S. Pat. No. 7,157,414). Surface tensiometry has shown that the hmp associates a fraction of the surfactant to the hydrophobic domains of the polymer thereby reducing the free micelle concentration.

US 2008/0113895 describes the use of low molecular weight acrylic polymers with the anionic surfactants sodium laureth sulfate and sodium trideceth sulfate for mild cleansing systems.

U.S. Pat. No. 5,130,056 relates to a washing agent, cleansing agent and/or toiletry containing at least one ionic and/or amphoteric surfactant and at least one $C_8$ to $C_{18}$ fatty acid monoester of diglycerol and/or $C_8$ to $C_{18}$ fatty acid diester of tetraglycerol as a constituent of the mixture, 2 to 30% by weight, preferably 10 to 20% by weight, of at least one fatty acid monoester of diglycerol and/or fatty acid diester of tetraglycerol, relative to the total surfactant content (100% by weight), being present in the surfactant mixture.

However, these high molecular weight hydrophobically modified polymers lose significant efficiency at high polymer concentrations, that is to say as the hmp concentration is increased, the mildness benefit gets smaller and smaller.

US 2008/0112913 describes the use of low molecular weight acrylic polymers for irritation mitigation and points out the difficulty in creating clear cleansing systems with low molecular weight hydrophobically modified polymers.

More recently, low molecular weight hmp's have been shown to suffer less loss of efficiency compared with higher molecular weight hmp's (See U.S. Pat. No. 7,803,403). M. Fevola, r. Walters, J. LiBrizzi, "A New Approach to Formulating Mild Cleansers: Hydrophobically-Modified Polymers for Irritation Mitigation" *Polymeric Delivery of Therapeutics,* 2010, 221.) By reducing the molecular weight of the hmp, the polymer can more readily open into an expanded coil and therefore associate more surfactant even at higher polymer concentrations. Walters et al further demonstrated that this associated surfactant is in a more stable state, and the surfactant is less dynamic (co-pending U.S. patent application Ser. No. 12/779,211).

We have shown that low molecular weight hmp associates some fraction of the surfactant in the surfactant system, typically between 20-30%. The remainder of the surfactant is not associated to the polymer and exists as either free micelles or monomeric surfactant. With the low molecular weight hmp present, the surfactant exists in three states: 1) associated to the polymer 2) in a free micelle, or 3) as monomeric surfactant. The low molecular weight hmp only affects the surfactant that is associated to the polymer, so that the only mildness improvement to the formula is due to the surfactant associated to the polymer.

Even when the low molecular weight hmp is present, there are still many free micelles in solution that can contribute to the aggressiveness of the surfactant solution.

The skin care compositions of this invention have low irritation characteristics and are capable of exhibiting superior foaming, which is desirable in a cleansing composition.

SUMMARY OF THE INVENTION

Figure 1:
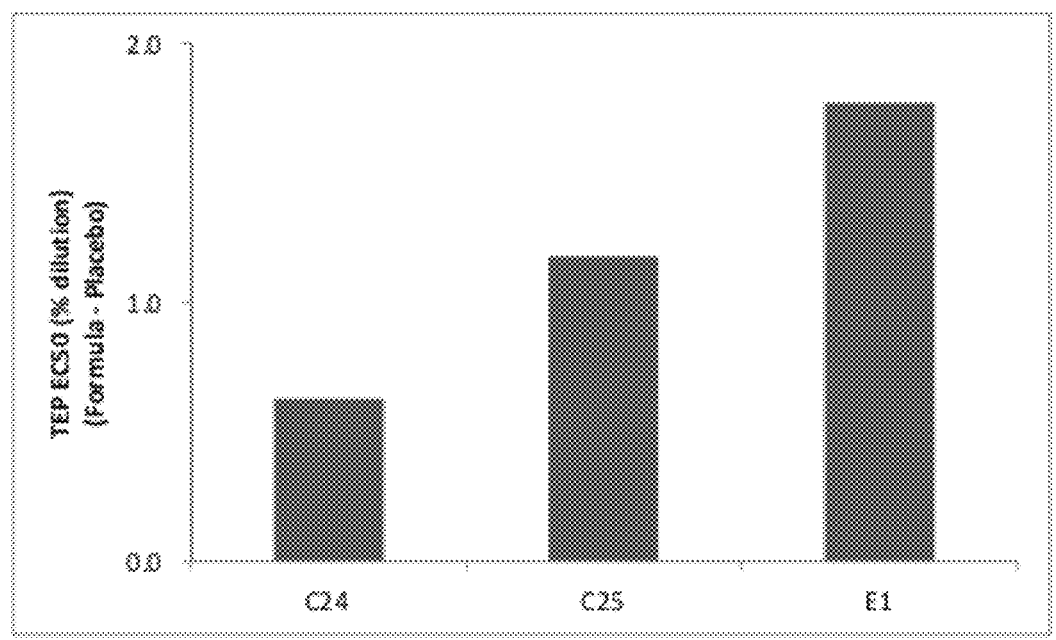
FIG. 1 illustrates the difference in TEP test EC50 of formulations set forth in Example 3 compared with placebo.
Figure 2:
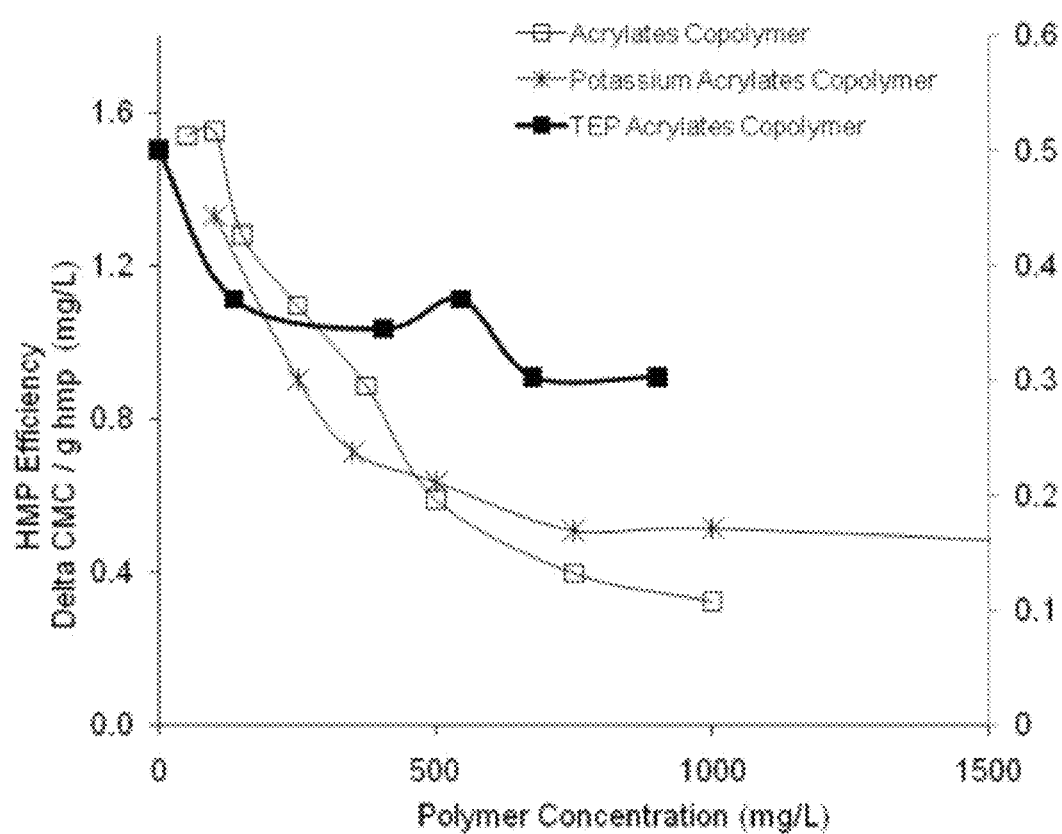
FIG. 2 illustrates hydrophobically-modified polymer efficiency as a function of polymer concentration for three different copolymers.

The compositions of this invention relate to skin cleansing compositions comprising, consisting essentially of, and consisting of:

(a) a low molecular weight, non-crosslinked, linear acrylic copolymer;
(b) an ester of a fatty acid and a glycerin polymer, wherein said ester has x glycerin repeat units and a carbon chain length of n, wherein x is from 8 to 14; and n is from 10 to 18; and
(c) at least one surfactant selected from the group consisting of an anionic surfactant and an amphoteric or a mixture thereof.

One or more polyglyceryl esters (hereinafter, "PGE") added to the cleansing compositions of this invention likely enter free micelles existing in the compositions that are left unassociated with low molecular weight HMP. The PGE acts to stabilize and render milder the free micelles that are left in the surfactant system. Because free micelles make up the surfactant population that is responsible for the majority of the aggressiveness of the surfactant system when the low molecular weight HMP is present in the compositions, the PGE's action in rendering these free micelles milder permits the entire cleansing system to become significantly milder than if the PGE were not present in the composition.

DETAILED DESCRIPTION OF THE INVENTION

We have discovered that the compositions of the invention exhibit a unique and unexpected combination of properties including relatively low irritation and relatively high foaming characteristics. This makes the compositions of this invention highly desirable for skin care, including baby and infant skin, cosmetic or cleansing compositions. The compositions of this invention contain, comprise, consist essentially or consist of a low molecular weight, non-crosslinked, linear acrylic copolymer, polyglyceryl esters and at least one anionic or amphoteric surfactant and/or combinations thereof.

Surprisingly, using a select group of surfactants to bind with low molecular weight, non-crosslinked, linear acrylic copolymer, results in a composition that is milder than previously thought would be possible.

The addition of a low molecular weight hmp to surfactant system has been shown to result in a milder surfactant that still retains foaming performance (M. Fevola, r. Walters, J. LiBrizzi, "A New Approach to Formulating Mild Cleansers: Hydrophobically-Modified Polymers for Irritation Mitigation" *Polymeric Delivery of Therapeutics*, 2010, 221). The low molecular weight hmp will associated a fraction of the surfactant to the hydrophobic domains of the polymer. This associated surfactant is in a more stable state than the surfactant that exists in free micelles, and the surfactant is less dynamic that surfactant that exists in free micelles.

As used herein, the term "pH" shall include pH measurements as determined by ASTM method E70-07 Standard Test Method for pH of Aqueous Solutions With the Glass Electrode.

As used herein, the term "foaming cleansing composition" includes those compositions that have the ability to remove lipids, oils and natural components from the skin surface and which produce a foam (i.e., a system of bubbles surrounded by film). A cleansing composition is typically applied to the skin and rinsed off with water. Rubbing with the fingers, hands or wash cloth or pouring into a bath may result in sudsing or foaming of the cleanser. If the skin has an impaired barrier prior to cleansing and exposure to foaming cleansing composition, certain types of cleansing compositions can be further damaging to the health and integrity of the skin barrier already in distress. In particular, cleansing compositions containing a relatively high surfactant content will tend to be more damaging to the skin barrier function.

In particular, skin cleansing formulations contain surfactants that emulsify soils on the skin surface for removal with a water rinse. Surfactants useful in the compositions of this invention may be anionic, amphoteric and may be in the form of a bar, a liquid, a cream, a gel or the like. Surfactants vary markedly in their effects on the skin and differ significantly in their effect on the skin barrier. They have been shown to vary in their effects on corneocyte swelling, disaggregation, and damage. Surfactants, as well as other topical treatments, can vary greatly in their effects on the permeability barrier of skin.

Measuring the Impairment of Barrier Function

TEWL and skin hydration constitute two areas of measurements by which to determine whether skin barrier has been impaired. However, absolute measurements generated by these test methods may require additional means by which to understand the characteristics and extent of barrier impairment. For example, two different people may be exposed to the environment but present very different TEWL or skin hydration measurements from their exposed skin depending on the nature of their own particular skin properties. Likewise, different environments may produce similar TEWL or skin hydration measurements in very different people. Therefore, when determining the effect of the application of the compositions of this invention to skin having impaired barrier function, it is preferable to examine how the TEWL or skin hydration level may change upon exposure to cleansing compositions and measure the change in TEWL or skin hydration after exposure. In addition, TEWL and skin hydration may be linked to surfactant kinetics and dynamics.

It has been demonstrated that impaired skin barrier may have certain physical characteristics, including a higher TEWL, although decreased hydration level is not always initially present in skin having impaired barrier function. However, it is desirable, when cleansing skin with impaired barrier function, not to increase the transepidermal water loss and thereby cause additional impairment.

The hydration level of the stratum corneum affects its mechanical and electrical properties, thus the Ski-Con-200EX (I.B.S Co., LTD., Japan), which measures the high frequency conductivity of the skin, can be used to measure the relative water holding capacity of the superficial corneocytes (first layer). The measurement may be performed by placing a probe on the skin surface for a period of time. The probe is connected to a computer or other data recording device. Skin hydration measured via conductance is expressed as micro Siemans, "μS".

We have discovered that, surprisingly, it is possible to cleanse skin using compositions that are mild to the skin and which only minimally change the impairment of the skin barrier and yet are able to produce a level of foam acceptable to users.

Polymeric Material

As used herein the term "low molecular weight" polymer refers to a polymer having a number average molecular weight ($M_n$) as measured by gel permeation chromatography (GPC) calibrated with a poly(methyl methacrylate) (PMMA) standard of about 100,000 or less. In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

The polymeric material useful in the methods of this invention is preferably a composition suitable for associating anionic and/or amphoteric surfactant thereto and is a non-crosslinked, linear acrylic copolymer that mitigates the impaired dermal barrier damage typically associated with surfactant systems without substantially increasing viscosity build. The non-crosslinked, linear polymers are preferably of low molecular weight having a number average molecular weight of 100,000 or less as measured by gel permeation chromatography (GPC) calibrated with a poly(methyl methacrylate) (PMMA) standard (as used herein, unless otherwise specified, all number average molecular weights ($M_n$) refer to molecular weight measured in such manner). The copolymeric mitigant is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a $C_1$ to $C_9$ alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention the second monomeric component is represented by the formula:

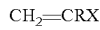

wherein R is hydrogen or methyl; X is —C(O)OR' or —OC(O)$R^2$; $R^1$ is linear or branched $C_1$ to $C_9$ alkyl; and $R^2$ is hydrogen or linear or branched $C_1$ to $C_9$ alkyl. In another aspect of the invention $R^1$ and $R^2$ is linear or branched $C_1$ to $C_8$ alkyl and in a further aspect $R^1$ and $R^2$ are linear or branched $C_2$ to $C_5$ alkyl.

Exemplary first monomeric components include (meth) acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof. As used herein, the term "(meth)acrylic" acid and "(meth)acrylate" are meant to include the corresponding methyl derivatives of acrylic acid and the corresponding alkyl acrylate For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one C1 to C9 alkyl (meth)acrylate.

The non-crosslinked, linear acrylic copolymer mitigants of the invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

In another aspect emulsion polymerization techniques can be used to synthesize the non-crosslinked, linear acrylic copolymer mitigants of the invention. In a typical emulsion polymerization, a mixture of the disclosed monomers is added with mixing agitation to a solution of emulsifying surfactant, such as, for example, an anionic surfactant (e.g., fatty alcohol sulfates or alkyl sulfonates), in a suitable amount of water, in a suitable reactor, to prepare a monomer emulsion. The emulsion is deoxygenated by any convenient method, such as by sparging with nitrogen, and then a polymerization reaction is initiated by adding a polymerization catalyst (initiator) such as sodium persulfate, or any other suitable addition polymerization catalyst, as is well known in the emulsion polymerization art. The polymerization medium is agitated until the polymerization is complete, typically for a time in the range of about 4 to about 16 hours. The monomer emulsion can be heated to a temperature in the range of about 70 to about 95° C. prior to addition of the initiator, if desired. Unreacted monomer can be eliminated by addition of more catalyst, as is well known in the emulsion polymerization art. The resulting polymer emulsion product can then be discharged from the reactor and packaged for storage or use. Optionally, the pH or other physical and chemical characteristics of the emulsion can be adjusted prior to discharge from the reactor. Typically, the product emulsion has a total solids content in the range of about 10 to about 50 wt. %. Typically, the total polymer content (polymer solids) of the product emulsion is in the range of about 15 to about 45 wt. %, generally not more than about 35 wt. %.

In one aspect, the number average molecular weight ($M_n$) of the linear copolymeric mitigants of the present invention as measured by gel permeation chromatography (GPC) calibrated with a poly(methyl methacrylate) (PMMA) standard is 100,000 or less. In another aspect of the invention, the molecular weight ranges between about 5,000 and about 80,000 $M_n$, in a further aspect between about 10,000 and 50,000 $M_n$, and in a still further aspect between about 15,000 and 40,000 $M_n$.

In one aspect of the invention, the linear copolymeric mitigants have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

Preferably, the low molecular weight, non-crosslinked linear acrylic copolymer is potassium acrylates copolymer.

Polyglyceryl Esters

A second element of the invention is PGE. A preferable PGE for use in the compositions of this invention is an ester of a fatty acid and a glycerin polymer as described below:

an ester of a fatty acid and a glycerin polymer, wherein said ester has x glycerin repeat units and a carbon chain length of n, wherein x=number of glycerin repeat units n=carbon chain length wherein the PGE contains an average of from about eight to about fourteen glycerin units (i.e. x is between 8 to 14) and a carbon chain from about 10 to about 18 carbon atoms (i.e. n is between 10 to 18). More preferably, x should be from about 10 to about 12. Most preferably, x should be ten. More preferably, n should be from about 12 to about 18. Most preferably, n should be from about 12 to about 16.

As used herein, the term "glyceryl repeat unit" refers to a repeat unit that is a structural derivative of glycerol ($C_3H_8O_3$), such as repeat units corresponding to dehydrated glycerol ($C_3H_6O_2$). Examples of glycerine repeat units include:

(a) linear-1,4 ($L_{1,4}$) repeat units of the formula:

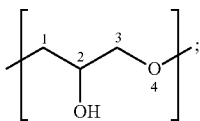

(b) linear-1,3 ($L_{1,3}$) PG repeat units of the formula:

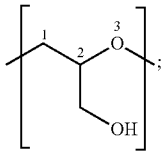

(c) dendritic (D) PG repeat units, which lead to branched and cyclic PGs, of the formula:

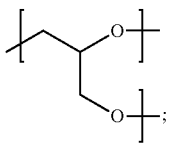

(d) terminal-1,2 ($T_{1,2}$) units (shown attached to a polyglyceryl moiety PG) of the formula:

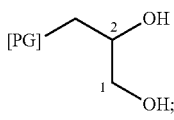

and
and (e) terminal-1,3 ($T_{1,3}$) units (shown attached to a polyglyceryl moiety PG) of the formula:

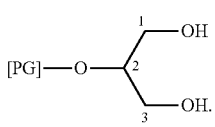

As used herein, a "polyglyceryl moiety" means a linear, branched, and/or cyclic polyether moiety comprising two or more glycerine repeat units. Polyglyceryl moieties may be derived via any of a variety of synthetic routes, including but not limited to condensation polymerization of glycerol, ring-opening polymerization of glycerol carbonate, and ring-opening polymerization of glycidol. In certain embodiments, polyglyceryl moieties comprise homopolyethers wherein all of the repeat units are glycerine repeat units. In certain other embodiments, the polyglyceryl moieties are copolyethers, that is, they comprise both glycerine repeat units and additional polyether repeat units that are not glycerine repeat units. For example, glycerol may be copolymerized with 1,3-propanediol to yield a copolyether comprising both glycerine repeat units described above and oxypropylene repeat units of the formula:

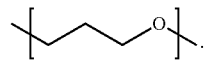

In the formulae herein and above, a polyglyceryl moiety is represented by "PG".

As used herein, the term "polyglyceryl nonionic surfactant" means an amphiphilic molecule comprising one or more nonionic hydrophilic segments comprised of a polyglyceryl moiety and one or more hydrophobic moieties. Examples of polyglyceryl nonionic surfactants include, but are not limited to, polyglyceryl esters (PGEs), such as Polyglyceryl-10 Laurate where PG=polyglyceryl moiety comprising ten (10) glycerine repeat units, and R=$C_{11}H_{23}$

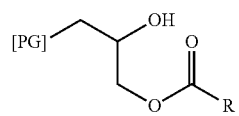

as well as, Polyglyceryl-10 Caprylate/Caprate, Polyglyceryl-10 Cocoate, Polyglyceryl-10 Myristate, Polyglyceryl-10 Palmitate, Polyglyceryl-10 Oleate, Polyglyceryl-12 Laurate, and the like. PGEs of the present invention may include polyglyceryl moities bearing multiple ester substitutions (i.e. the PGEs may be monoesters, diesters, triesters, and the like).

Other polyglyceryl nonionic surfactants include polyglyceryl ethers, such as Polyglyceryl-10 Lauryl Ether, where PG=polyglyceryl moiety comprising 10 glycerine repeat units, and R=$C_{12}H_{25}$:

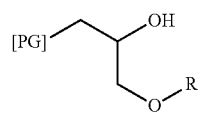

and the like. Still other polyglyceryl nonionic surfactants include polyglyceryl sorbitan fatty acid esters, such as Polyglyceryl-20 Sorbitan Laurate, where PG=polyglycerol, the sum of all PG RUs=20, and R=$C_{11}H_{23}$. (see Bevinakatti, et al. WO 2009016375, assigned to Croda International PLC)

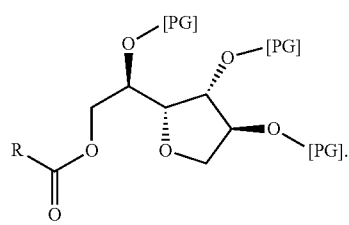

Any suitable polyglyceryl nonionic surfactants may be used in the compositions of the present invention. In certain preferred embodiments, the polyglyceryl nonionic surfactants are selected from the group consisting of polyglyceryl esters, polyglyceryl ethers, polyglyceryl sorbitan fatty acid esters, combinations of two or more thereof and the like. In certain more preferred embodiments, the polyglyceryl nonionic surfactants are selected from the group consisting of polyglyceryl esters, polyglyceryl ethers, and combinations of two or more thereof.

The PGE may be the reaction product of a polyol and a monoglyceride, diglyceride, triglyceride, or a mixture thereof where the reaction product may comprise a transesterification product. The polyol may be selected from glycerol, ethylene glycol, polyethylene glycol, sorbitol, propylene glycol, pentaerythritol, a saccharide, or a mixture thereof.

In certain other preferred embodiments, the compositions of the invention comprise, consist essentially of or consist of PGE's selected from the group consisting of: Polyglyceryl-8 Caprylate/Caprate, Polyglyceryl-8 Laurate, Polyglyceryl-9 Laurate, Polyglyceryl-10 Laurate, Polyglyceryl-8 Cocoate, Polyglyceryl-9 Cocoate, Polyglyceryl-10 Cocoate, Polyglyceryl-11 Cocoate, Polyglyceryl-12 Cocoate, Polyglyceryl-8 Myristate, Polyglyceryl-9 Myristate, Polyglyceryl-10 Myristate, Polyglyceryl-11 Myristate, Polyglyceryl-12 Myristate, Polyglyceryl-8 Palmitate, Polyglyceryl-9 Palmitate, Polyglyceryl-10 Palmitate, Polyglyceryl-11 Palmitate, Polyglyceryl-12 Palmitate, Polyglyceryl-10 Oleate, Polyglyceryl-11 Oleate, Polyglyceryl-12 Oleate, Polyglyceryl-10 Stearate, Polyglyceryl-12 Stearate, Polyglyceryl-14 Stearate and Polyglyceryl-14 Oleate and combinations of two or more thereof.

We have found that certain PGE's are not effective for use in the compositions of our invention, including the following:

Polyglyceryl-6 Cocoate, Polyglyceryl-4 Caprylate/Caprate, Polyglyceryl-5 Caprylate/Caprate, Polyglyceryl-6 Caprylate/Caprate, Polyglyceryl-7 Caprylate/Caprate, Polyglyceryl-4 Laurate, Polyglyceryl-5 Laurate, Polyglyceryl-6 Laurate, Polyglyceryl-7 Laurate, Polyglyceryl-6 Myristate and Polyglyceryl-7 Myristate, Polyglyceryl-8 Oleate, Polyglyceryl-14 Laurate.

We have found that the PGE should be sufficiently hydrophobic to co-micellize with other surfactants present in the compositions of this invention. Also the PGE must be sufficiently hydrophilic to be water dispersible. Therefore, preferably, the ratio of x:n is less than about 2 and greater than about 1.

Most preferably, a PGE suitable for use in the compositions of the invention include the following: Polyglyceryl-10 Laurate, Polyglyceryl-10 Cocoate, Polyglyceryl-11 Cocoate, Polyglyceryl-12 Cocoate, Polyglyceryl-10 Myristate, Polyglyceryl-11 Myristate, Polyglyceryl-12 Myristate, Polyglyceryl-10 Palmitate, Polyglyceryl-11 Palmitate, Polyglyceryl-12 Palmitate, Polyglyceryl-10 Oleate, Polyglyceryl-11 Oleate, Polyglyceryl-12 Oleate, Polyglyceryl-10 Stearate, Polyglyceryl-11 Stearate, and Polyglyceryl-12 Stearate.

Most preferably, polyclyceryl-10 laurate is present in the compositions of this invention, having the following structure:

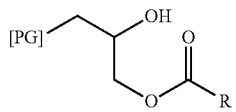

Wherein PG=polyglyceryl moiety comprising ten (10) glycerine repeat units, and R=$C_{11}H_{23}$.

Surfactant

A third element of the present invention is an anionic or amphoteric surfactant.

According to certain embodiments, suitable anionic surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof. Examples of certain preferred anionic surfactants include:

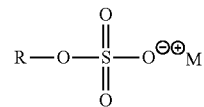

where R=$C_8$-$C_{24}$ alkyl (linear or branched, saturated or unsaturated) or mixtures thereof and $M^+$=monovalent cation. Examples include Sodium Lauryl Sulfate (R=$C_{12}$ alkyl, $M^+$=$Na^+$), Ammonium Lauryl Sulfate (R=$C_{12}$ alkyl, $M^+$=$NH_3^+$), and Sodium Coco-Sulfate (R=coconut alkyl, $M^+$=$Na^+$);

Alkyl Ether Sulfates

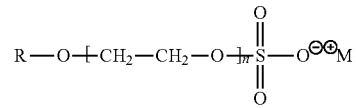

where R=$C_8$-$C_{24}$ alkyl (linear or branched, saturated or unsaturated) or mixtures thereof, n=1-12, and $M^+$=monovalent cation. Examples include Sodium Laureth Sulfate (R=$C_{12}$ alkyl, $M^+$=$Na^+$, n=1-3), Ammonium Laureth Sulfate (R=$C_{12}$ alkyl, $M^+$=$NH_3^+$, n=1-3), and Sodium Trideceth Sulfate (R=$C_{13}$ alkyl, $M^+$=$Na^+$, n=1-4);

Alkyl Monoglyceride Sulfates

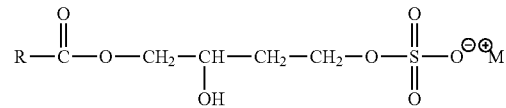

where R=$C_8$-$C_{24}$ alkyl (linear or branched, saturated or unsaturated) or mixtures thereof and $M^+$=monovalent cation. Examples include Sodium Cocomonoglyceride Sulfate (RCO=coco acyl, $M^+$=$Na^+$) and Ammonium Cocomonoglyceride Sulfate (RCO=coco acyl, $M^+$=$NH_3$);

Alkyl Carboxylates

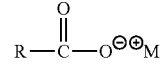

where R=$C_8$-$C_{24}$ alkyl (linear or branched, saturated or unsaturated) or mixtures thereof and $M^+$=monovalent cation. Examples include Sodium Laurate (R=$C_{11}H_{23}$, $M^+$=$Na^+$) and Potassium Myristate (R=$C_{13}H_{27}$, $M^+$=$K^+$);

Alkyl Ether Carboxylates

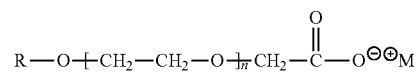

where R=$C_8$-$C_{24}$ alkyl (linear or branched, saturated or unsaturated) or mixtures thereof, n=1-20, and $M^+$=monovalent cation. Examples include Sodium Laureth-13 Carboxylate (R=$C_{12}$ alkyl, $M^+$=$Na^+$, n=13), and Sodium Laureth-3 Carboxylate (R=$C_{12}$ alkyl, $M^+$=$Na^+$, n=3); Alpha olefin sulfonates prepared by sulfonation of long chain alpha olefins. Alpha olefin sulfonates consist of mixtures of alkene sulfonates,

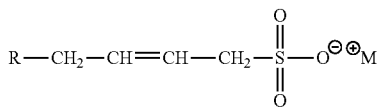

where R=$C_8$-$C_{18}$ alkyl or mixtures thereof and $M^+$=monovalent cation, and hydroxyalkyl sulfonates,

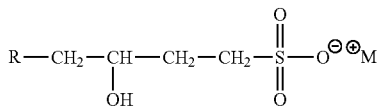

where R=$C_4$-$C_{18}$ alkyl or mixtures thereof and $M^+$=monovalent cation. Examples include Sodium C12-14 Olefin Sulfonate (R=$C_8$-$C_{10}$ alkyl, $M^+$=$Na^+$ and Sodium C14-16 Olefin Sulfonate (R=$C_{10}$-$C_{12}$ alkyl, $M^+$=$Na^+$);

Alkyl Sulfonates:

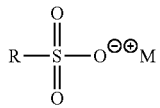

where R=$C_8$-$C_{24}$ alkyl (linear or branched, saturated or unsaturated) or mixtures thereof and $M^+$=monovalent cation. Examples include Sodium C13-17 Alkane Sulfonate (R=$C_{13}$-$C_{17}$ alkyl, $M^+$=$Na^+$ and Sodium C14-17 Alkyl Sec Sulfonate (R=$C_{14}$-$C_{17}$ alkyl, $M^+$=$Na^+$);

Alkylaryl Sulfonates

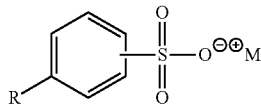

where R=$C_6$-$C_{18}$ alkyl (linear or branched, saturated or unsaturated) or mixtures thereof and $M^+$=monovalent cation. Examples include Sodium Deceylbenzenesulfonate (R=$C_{10}$ alkyl, $M^+$=$Na^+$ and Ammonium Dodecylbenzensulfonate (R=$C_{12}$ alkyl, $M^+$=$NH_3^+$);

Alkyl Glyceryl Ether Sulfonates:

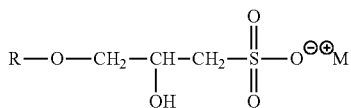

where R=$C_8$-$C_{24}$ alkyl (linear or branched, saturated or unsaturated) or mixtures thereof and $M^+$=monovalent cation, such as Sodium Cocoglyceryl Ether Sulfonate (R=coco alkyl, $M^+$=$Na^+$);

Alkyl Sulfosuccinates

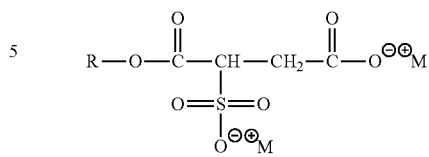

Where R=$C_8$-$C_{20}$ alkyl (linear or branched, saturated or unsaturated) or mixtures thereof and $M^+$=monovalent cation, such as Disodium Lauryl Sulfosuccinate (R=lauryl, $M^+$=$Na^+$).

Alkyl Ether Sulfosuccinates

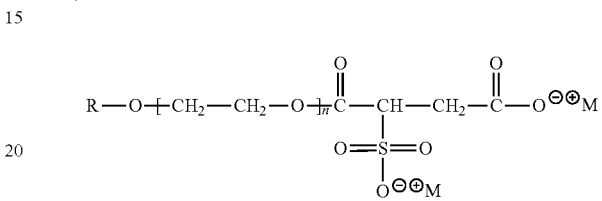

Where R=$C_8$-$C_{20}$ alkyl (linear or branched, saturated or unsaturated) or mixtures thereof, n=1-12, and $M^+$=monovalent cation, such as Disodium Laureth Sulfosuccinate (R=lauryl, n=1-4, and $M^+$=$Na^+$)

Dialkyl Sulfosuccinates

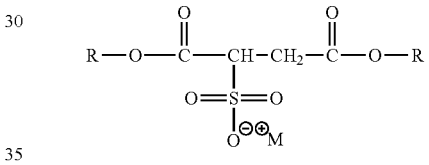

Where R=$C_6$-$C_{20}$ alkyl (linear or branched, saturated or unsaturated) or mixtures thereof and $M^+$=monovalent cation, such as Diethylhexyl Sodium Sulfosuccinate (R=2-ethylhexyl, $M^+$=$Na^+$).

Alkylamidoalkyl Sulfosuccinates

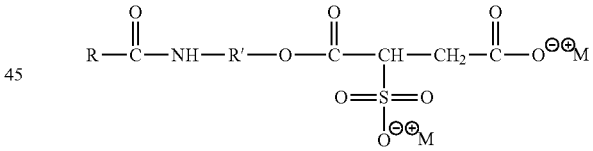

Where R=$C_8$-$C_{20}$ alkyl (linear or branched, saturated or unsaturated) or mixtures thereof, R'=$C_2$-$C_4$ alkyl (linear or branched), and $M^+$=monovalent cation, such as Disodium Cocamido MIPA-Sulfosuccinate (RCO=coco acyl, R'=isopropyl, $M^+$=$Na^+$).

Alkyl Sulfosuccinamates

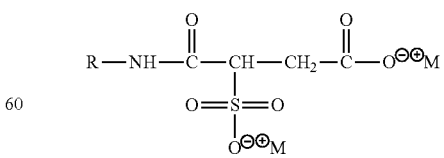

Where R=$C_8$-$C_{20}$ alkyl (linear or branched, saturated or unsaturated) or mixtures thereof and $M^+$=monovalent cation, such as Disodium Stearyl Sulfosuccinamate (R=stearyl, $C_{18}H_{37}$, $M^+$=$Na^+$).

Alpha-Sulfo Fatty Acid Esters

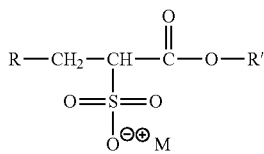

Where R=$C_6$-$C_{16}$ alkyl (linear or branched, saturated or unsaturated) or mixtures thereof, R'=$C_1$-$C_4$ alkyl, and $M^+$=monovalent cation, such as Sodium Methyl 2-Sulfolaurate (R=$C_{10}H_{21}$, R'=methyl, $CH_3$, and $M^+$=$Na^+$).

Alpha-Sulfo Fatty Acid Salts

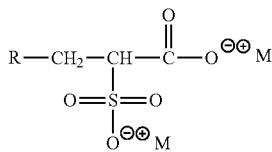

Where R=$C_6$-$C_{16}$ alkyl (linear or branched, saturated or unsaturated) or mixtures thereof, $M^+$=monovalent cation, such as Disodium 2-Sulfolaurate (R=$C_{10}H_{21}$, $M^+$=$Na^+$).

Alkyl Sulfoacetates

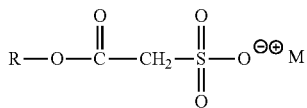

Where R=$C_8$-$C_{18}$ alkyl (linear or branched, saturated or unsaturated) or mixtures thereof, $M^+$=monovalent cation, such as Sodium Lauryl Sulfoacetate (R=lauryl, $C_{12}H_{25}$, $M^+$=$Na^+$).

Acyl Isethionates

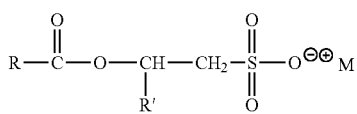

where RCO=$C_8$-$C_{20}$ acyl (linear or branched, saturated or unsaturated) or mixtures thereof, R'=H or $CH_3$, $M^+$=monovalent cation, such as Sodium Cocoyl Isethionate (RCO=coco acyl, R'=H, $M^+$=$Na^+$ and Sodium Lauroyl Methyl Isethionate (RCO=lauroyl, R'=$CH_3$, $M^+$=$Na^+$).

Acyl Lactylates

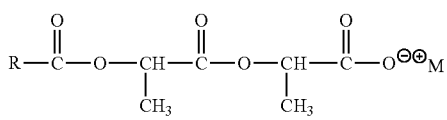

where RCO=$C_8$-$C_{20}$ acyl (linear or branched, saturated or unsaturated) or mixtures thereof, $M^+$=monovalent cation, such as Sodium Lauroyl Lactylate (RCO=lauroyl, $M^+$=$Na^+$).

Acyl Glycinates and Acyl Sarcosinates

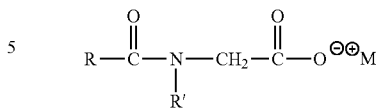

where RCO=$C_8$-$C_{20}$ acyl (linear or branched, saturated or unsaturated) or mixtures thereof, R'=H (glycinate) or $CH_3$ (sarcosinate), $M^+$=monovalent cation, such as Sodium Cocoyl Glycinate (RCO=coco acyl, R'=H, $M^+$=$Na^+$), Ammonium Cocoyl Sarcosinate (RCO=coco acyl, R'=$CH_3$, $M^+$=$NH_4^+$) and Sodium Lauroyl Sarcosinate (RCO=lauroyl, R'=$CH_3$, $M^+$=$Na^+$).

Acyl Glutamates

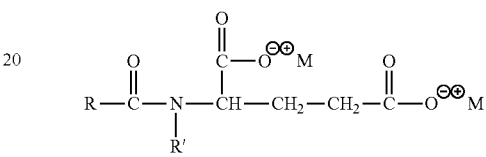

where RCO=$C_8$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, $M^+$=$Na^+$) and Disodium Lauroyl Glutamate (RCO=lauroyl, R'=H, $M^+$=$Na^+$).

Acyl Aspartates

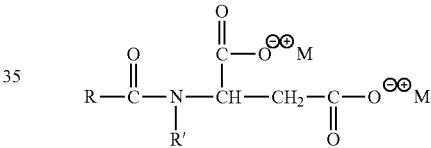

Where RCO=$C_8$-$C_{20}$ acyl (linear or branched, saturated or unsaturated) or mixtures thereof, R'=H or $CH_3$, $M^+$=monovalent cation, such as Disodium N-Lauroyl Aspartate (RCO=lauroyl, R'=H, $M^+$=$Na^+$).

Acyl Taurates

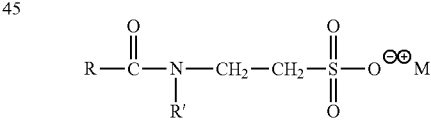

where RCO=$C_6$-$C_{20}$ acyl (linear or branched, saturated or unsaturated) or mixtures thereof, R'=H or $CH_3$, $M^+$=monovalent cation, such as Disodium Cocoyl Glutamate (RCO=coco acyl, R'=H, $M^+$=$Na^+$) and Disodium Lauroyl Glutamate (RCO=lauroyl, R'=H, $M^+$=$Na^+$).

Alkyl Phosphates

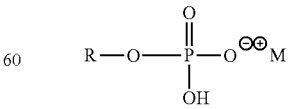

Where R=$C_6$-$C_{20}$ alkyl (linear or branched, saturated or unsaturated) or mixtures thereof and $M^+$=monovalent cation, such as Potassium Lauryl Phosphate (R=lauryl, $C_{12}H_{25}$, $M^+$=$K^+$) and Potassium C12-13 Alkyl Phosphate (R=$C_{12}$-$C_{13}$ alkyl, $M^+$=$K^+$)

Anionic derivatives of alkyl polyglucosides (APGs), including: Sodium Lauryl Glucoside Carboxylate, Disodium Coco-Glucoside Citrate, Sodium Coco-Glucoside Tartrate, Disodium Coco-Glucoside Sulfosuccinate, Sodium Cocoglucosides Hydroxypropylsulfonate, Sodium Decylglucosides Hydroxypropylsulfonate, Sodium Laurylglucosides Hydroxypropylsulfonate, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer; and anionic polymeric APG derivatives, such as those described in O'Lenick, U.S. Pat. Nos. 7,507,399; 7,375,064; and 7,335,627), and combinations of two or more thereof, and the like.

Amphoteric Surfactants

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Examples of amphoteric surfactants suitable for use in the present invention include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

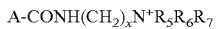
A-CONH(CH$_2$)$_x$N$^+$R$_5$R$_6$R$_7$ wherein
A is an alkyl or alkenyl group having from about 7 to about 21, e.g. from about 10 to about 16 carbon atoms;
x is an integer of from about 2 to about 6;
R$_5$ is hydrogen or a carboxyalkyl group containing from about 2 to about 3 carbon atoms;
R$_6$ is a hydroxyalkyl group containing from about 2 to about 3 carbon atoms or is a group of the formula:

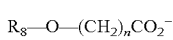
R$_8$—O—(CH$_2$)$_n$CO$_2^-$ wherein
R$_8$ is an alkylene group having from about 2 to about 3 carbon atoms and n is 1 or 2; and
R$_7$ is a carboxyalkyl group containing from about 2 to about 3 carbon atoms;

Examples of suitable alkyl betaines include those compounds of the formula:

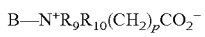
B—N$^+$R$_9$R$_{10}$(CH$_2$)$_p$CO$_2^-$ wherein
B is an alkyl or alkenyl group having from about 8 to about 22, e.g., from about 8 to about 16 carbon atoms;

R$_9$ and R$_{10}$ are each independently an alkyl or hydroxyalkyl group having from about 1 to about 4 carbon atoms; and
p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

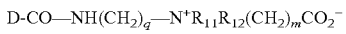
D-CO—NH(CH$_2$)$_q$—N$^+$R$_{11}$R$_{12}$(CH$_2$)$_m$CO$_2^-$ wherein
D is an alkyl or alkenyl group having from about 7 to about 21, e.g. from about 7 to about 15 carbon atoms;
R$_{11}$ and R$_{12}$ are each independently an alkyl or
Hydroxyalkyl group having from about 1 to about 4
carbon atoms;
q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

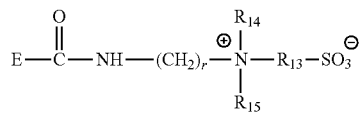

wherein
E is an alkyl or alkenyl group having from about 7 to about 21, e.g. from about 7 to about 15 carbon atoms;
R$_{14}$ and R$_{15}$ are each independently an alkyl, or hydroxyalkyl group having from about 1 to about 4 carbon atoms;
r is an integer from about 2 to about 6; and
R$_{13}$ is an alkylene or hydroxyalkylene group having from
about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

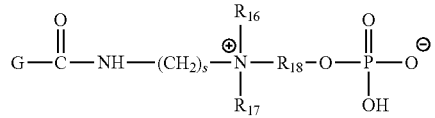

wherein
G is an alkyl or alkenyl group having about 7 to about 21, e.g. from about 7 to about 15 carbon atoms;
s is an integer from about 2 to about 6;
R$_{16}$ is hydrogen or a carboxyalkyl group containing from about 2 to about 3 carbon atoms;
R$_{17}$ is a hydroxyalkyl group containing from about 2 to about 3 carbon atoms or a group of the formula:

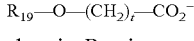
R$_{19}$—O—(CH$_2$)$_t$—CO$_2^-$ wherein R$_{19}$ is an alkylene or hydroxyalkylene group having from about 2 to about 3 carbon atoms and t is 1 or 2; and $R_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

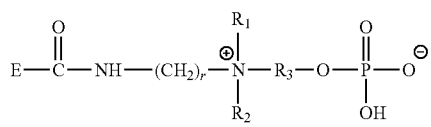

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

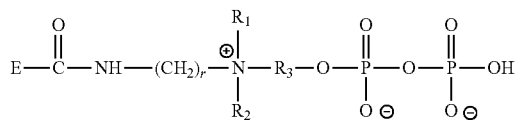

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

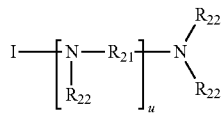

wherein
  I is an alkyl or alkenyl group containing from about 8 to about 22, e.g. from about 8 to about 16 carbon atoms;
  $R_{22}$ is a carboxyalkyl group having from about 2 to about 3 carbon atoms;
  $R_{21}$ is an alkylene group having from about 2 to about 3 carbon atoms and
  u is an integer from about 1 to about 4.

Any suitable amounts of polymeric material, PGE and anionic and/or amphoteric surfactants may be used in accord with the compositions and methods of this invention. In certain preferred embodiments, the compositions of this invention comprise, consist essentially of and consist of from greater than about 0.02 to about 5 weight percent of polymeric material (based on active amount of polymeric material in the total weight of composition). In certain more preferred embodiments, the compositions comprise from about 0.1 to about 3 weight percent of polymeric material, more preferably from about 0.1 to about 2 weight percent of polymeric material, and even more preferably from about 0.2 to about 1.2 weight percent of polymeric material.

In certain preferred embodiments, the compositions of this invention comprise, consist essentially of and consist of from greater than about 1.5 to less than about 15 weight percent of total surfactants based on total active amount of surfactant(s) in the total weight of composition. In certain more preferred embodiments, the compositions comprise from about 2 to about 7 weight percent of total surfactants (either amphoteric or anionic or the combination there of). Preferred embodiment formulas have from about 1.5 to about 5 weight percent total surfactant.

The non-crosslinked, linear acrylic copolymers useful in the compositions of this invention can be synthesized via free radical polymerization techniques known in the art. In one aspect of the invention, the amount of the first monomeric component to the second monomeric component utilized ranges from about 20:80 wt. % to about 50:50 wt. %, based on the total weight of all of the monomers in the polymerization medium. In another aspect the weight ratio of the first monomeric component to the second monomeric component is about 35:65 wt. %, and in a further aspect the weight ratio of first monomeric component to second monomeric component is about 25:75 wt. %, all based on the total weight of all monomers in the polymerization medium.

The cleansing compositions produced, as well as any of the compositions containing polymeric material, PGE and at least one anionic and/or amphoteric surfactant that are combined in the combining step according to the present methods may further comprise any of a variety of other components nonexclusively including one or more amphoteric, nonionic and/or cationic surfactants, pearlescent or opacifying agents, thickening agents, secondary conditioners, humectants, chelating agents, and additives which enhance the appearance, feel and fragrance of the compositions, such as colorants, fragrances, preservatives, pH adjusting agents and the like.

Any of a variety of commercially available secondary conditioners, such as volatile silicones, which impart additional attributes, such as gloss to the hair should be suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Any of a variety of commercially available humectants, which are capable of providing moisturization and conditioning properties to the personal cleansing composition, is suitable for use in the compositions of this invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—(R"O)$_b$—H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—

(OCH$_2$CH$_2$)$_c$—OH, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include organic acid preservatives may include benzoic acid and alkali metal and ammonium salts thereof (e.g. sodium benzoate), sorbic acid and alkali metal and ammonium salts thereof (e.g. potassium sorbate), p-Anisic acid and alkali metal and ammonium salts thereof, and salicylic acid and alkali metal and ammonium salts thereof. The pH of the composition may be adjusted to the appropriate acidic value using any cosmetically acceptable organic or inorganic acid, such as citric acid, acetic acid, glycolic acid, lactic acid, malic acid, tartaric acid, or hydrochloric acid.

Sodium benzoate may be present in the composition as a preservative in an amount effective to preserve the composition, based upon the total weight of the composition, from about 0 to about 0.5 percent. Potassium sorbate is another preservative compound that may be present in the composition in an amount, based upon the total weight of the composition, from about 0 to about 0.6 percent, more preferably from about 0.3 to about 0.5 percent.

The methods of this invention may further comprise any of a variety of steps for mixing or introducing one or more of the optional components described hereinabove with or into a composition comprising a polymeric material and/or an anionic and/or amphoteric surfactant before, after, or simultaneously with the combining step described above. While in certain embodiments, the order of mixing is not critical, it is preferable, in other embodiments, to pre-blend certain components, such as the fragrance and the nonionic surfactant before adding such components into a composition comprising a polymeric material and/or an anionic surfactant.

The cleansing methods of the present invention may further comprise any of a variety of additional, optional steps associated conventionally with cleansing hair and skin including, for example, lathering, rinsing steps, and the like.

Although applicants do not wish to be bound by or to any particular theory of operation, it is believed that surfactant associated with the low molecular weight hydrophobically-modified polymer (hm-polymer) is more stable than surfactants that exist as a micelle. Thus, surfactant contained in a micelle structure more readily disperses out of the micelle than it does when associated with low molecular weight hydrophobically-modified polymer.

The foregoing information regarding low molecular weight hydrophobically-polymers as well as compositions that may be useful in the methods of this invention are set forth in US2008/0112913, US2006/0257348, and US20070111910, all of which are hereby incorporated herein by reference.

The methods and compositions of this invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

Methods
Equilibrium Tensiometry Test

The Tensiometry test may be used to determine the suitability of a particular hydrophobically-modified material for binding surfactant thereto. A method to measure the equilibrium surface tension, $\gamma_{eq}$, of surfactant solutions is the Wilhelmy plate method (Holmberg, K.; Jonsson, B.; Kronberg, B.; Lindman, B. Surfactants and Polymers in Aqueous Solution, Wiley & Sons, p. 347). In this method, a plate is submerged into a liquid and the downward force exerted by of the liquid on the plate is measured. The surface tension of the liquid can then be determined based on the force on the plate and the dimensions of the plate. By measuring the surface tension over a range of concentrations the critical micelle concentration (CMC) can then be determined.

In the following examples, a Kruss K100 Tensiometer (Kruss USA, Mathews, N.C.) with a platinum Wilhelmy plate used to determine the equilibrium surface tension of each sample over a range of concentrations. A sample vessel contains some initial solution in which the Wilhelmy plate measures the surface tension. Then a second solution is dosed into the sample vessel, stirred, and then probed again with the Wilhelmy plate.

Molecular Weight Determination

The number average ($M_n$) of the polymer samples are determined via the GPC method using a PL-220 high temperature GPC instrument manufactured by Polymer Laboratories. The instrument is integrated with a Compaq Dell OptiPlex GX270 computer with Waters Empower Pro LC/GPC software. Approximately 0.02 g polymer sample is dissolved in 5 ml of dimethyl actamide (DMAc), containing 250 ppm BHT and 0.05 molar NaNO$_3$. The test sample solution is gently shaken for about two hours and filtered with a 0.45 μm PTFE disposable disc filter. The chromatographic conditions are:

| | |
|---|---|
| Mobile phase: | DMAc, with 250 ppm BHT and 0.05 m NaNO$_3$, 70° C., 1.0 ml/min. |
| Sample size: | 100 μl |
| Column set: | PLgel (Guard + 2 × Mixed-B), all 10 μm, in series |
| Detector: | Refractive Index Detector |
| Calibration standard: | PMMA |

Skin Irritancy Potential Test Via In Vitro Skin Equivalents:

In vitro skin equivalents have been validated as a human skin model, and have effectively demonstrated a correlation between in vitro and in vivo effects of surfactants on skin as well as other consumer products. The EpiDerm™ Skin Model provided by MatTek Corporation was used in this study. The target cells are epithelial, derived from human skin. The test materials are applied directly to the culture surface, at air interface, so that undiluted and/or end use dilutions can be tested directly.

The experimental design used in this study consisted of a definitive assay to determine the release of one cytokine. Where tissue viability is not decreased by 50% as compared to the negative control tissue (as measured by MTT reduction), the inflammatory potential is then measured by the synthesis/release of the cytokine IL-1α.

In the treatment phase six skin equivalents are used for each diluted test product, individual results are averaged to provide overall response. 100 μl is applied to each equivalent for 1 hour of diluted product (10% dilution) exposure followed by 5 rinses of Ca, Mg Free PBS solution. Each Tissue is placed in a 6 well tray with assay medium for each rinse and returned to incubation for 24 hours. Following incubation tissues are assessed for cytokine responses of IL-1α.

Foam Volume Test:

An industrially accepted means to measure the foam generation of the consumer product is the Sita Foam Tester R-2000 (SITA Messtechnik GmbH, Dresden Germany). Specifically designed to measure foam generation, the Sita Foam Tester consists of a jacketed sample vessel with and agitator. To represent the hard water of tap water, 0.36 g of calcium chloride is dissolved in 995 g of DI water. Five (5) grams of test formula is added to this solution and mixed until homogeneous. Then this 0.5% dilution of test formula is placed in the holding tank of the Sita Foam Tester. For each experimental run, 250 ml of solution is introduced into the test vessel and allowed to come to 30° C.±2° C. The agitator spins at 1200 rpm or 900 rpm for 15 seconds, then the foam volume is measured. The agitation is repeated for a total of 12 cycles. The foam generation test is conducted 3 times for each test sample.

Trans-Epithelial Permeability Test ("TEP Test"):

The following Trans-Epithelial Permeability ("TEP") and Tensiometry tests are used in the instant methods and in the following Examples. In particular, as described above, the TEP test is used to determine when a composition is a reduced irritation composition according to the present invention.

Irritation to the eyes and/or skin expected for a given formulation is measured in accordance with the Invittox Protocol Number 86, the "Trans-epithelial Permeability (TEP) Assay" as set forth in Invittox Protocol Number 86 (May 1994), incorporated herein by reference. In general, the ocular and/or skin irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Example 1

Comparative Examples C1-C6

Preparation of Cleansing Compositions: Acrylates Copolymer Mildness Dose Response The cleansing compositions of C1-C6 were prepared as set forth below utilizing the materials and amounts listed in Table 1.

TABLE 1

Cleansing Compositions with HMP

| INCI Name | C1 | C2 | C3 | C4 | C5 | C6 |
|---|---|---|---|---|---|---|
| Acrylates Copolymer | — | 0.3 | 0.81 | 1.2 | 1.5 | 1.8 |
| Cocamidopropyl Betaine | 2.8 | 2.8 | 2.8 | 2.8 | 2.8 | 2.8 |
| Sodium Trideceth Sulfate | 6.00 | 6.00 | 6.00 | 6.00 | 6.00 | 6.00 |
| PEG-80 Sorbitan Laurate | 3.30 | 3.30 | 3.30 | 3.30 | 3.30 | 3.30 |
| Disodium Lauroamphodiacetate | 0.60 | 0.60 | 0.60 | 0.60 | 0.60 | 0.60 |
| Glycerin | 1.90 | 1.90 | 1.90 | 1.90 | 1.90 | 1.90 |
| Polyquaternium-10 | 0.14 | 0.14 | 0.14 | 0.14 | 0.14 | 0.14 |
| Quaternium-15 | 0.05 | 0.05 | 0.05 | 0.05 | 0.05 | 0.05 |
| Tetrasodium EDTA | 0.10 | 0.10 | 0.10 | 0.10 | 0.10 | 0.10 |
| Sodium Hydroxide | qs | qs | qs | qs | qs | qs |
| Water | qs | qs | qs | qs | qs | qs |

*expressed in % w/w

Each of the compositions of Table 1 was independently prepared as follows: Water (50.0 parts) was added to a beaker. For examples 1 through 6, Acrylates Copolymer (Carbopol Aqua SF-1, Lubrizol, Ohio) was added to the water with mixing. The PEG-80 Sorbitan Laurate was then added thereto with mixing, and the following ingredients were then added thereto independently with mixing until each respective resulting mixture was homogenous: Cocamidopropyl Betaine, Sodium Trideceth, Disodium Lauroamphodiacetate, Glycerin, Polyquaternium-10, Quaternium-15, and Tetrasodium EDTA. The pH of the resulting solution was then adjusted with a Sodium Hydroxide solution until a final pH of about 6.3 to 6.6 was obtained. The remainder of the water was then added thereto.

TEP Test Mildness Comparison of Cleansing Compositions:

The compositions prepared in accordance with Comparatives C1-C6 were then tested for mildness in accordance with the above TEP Test. Table 2 lists the TEP value of the composition of each Example:

TABLE 2

TEP Test Mildness Comparison

| Example | Hm-polymer concentration (w/w %) | TEP $EC_{50}$ (% dilution) | Delta TEP Value |
|---|---|---|---|
| C1 | 0.0 | 2.0 | — |
| C2 | 0.27 | 2.7 | 0.7 |
| C3 | 0.81 | 2.9 | 0.9 |
| C4 | 1.09 | 2.7 | 0.7 |
| C5 | 1.35 | 3.3 | 1.3 |
| C6 | 1.80 | 3.3 | 1.3 |

The addition of the HMP Acrylates Copolymer to the surfactant system increases the TEP test result C1 compared to C2, which indicated the surfactant system is rendered milder with the addition of Acrylates Copolymer. In Comparatives C2-C6, the concentration of Acrylates Copolymer is increased, and TEP test results are not observed to increase proportionally with the increase in Acrylates Copolymer concentration. The increase in the TEP test results undergoes a plateau with increasing concentrations of Acrylates Copolymer; there is a loss of efficiency of the Acrylates Copolymer to improve the mildness of the surfactant system at high Acrylates Copolymer concentrations.

The HMP, Acrylates Copolymer, approached a plateau of mildness improvement as measured by the TEP Test, at around 0.27% HMP.

Comparative Examples C7-C18

Preparation of HMP Solutions: Acrylates Copolymer and Potassium Acrylates Copolymer Tensiometry Dose Response The following example illustrates the efficiency of two HMP's to associate surfactant.
The cleansing compositions of C7-C18 were prepared according to the procedure set forth in Example 1 utilizing the materials and amounts listed in Table 3.

TABLE 3

| HMP solutions for Equilibrium Tensiometry test | | | | | | |
|---|---|---|---|---|---|---|
| INCI Name | C7 | C8 | C9 | C10 | C11 | C12 |
| Potassium Acrylates Copolymer | — | 0.010 | 0.025 | 0.035 | 0.050 | 0.075 |
| Sodium Hydroxide | qs | qs | qs | qs | qs | qs |
| DI Water | qs | qs | qs | qs | qs | qs |
| INCI Name | C13 | C14 | C15 | C16 | C17 | C18 |
| Acrylates Copolymer | — | 0.010 | 0.025 | 0.0375 | 0.050 | 0.075 |
| Sodium Hydroxide | qs | qs | qs | qs | qs | qs |
| DI Water | qs | qs | qs | qs | qs | qs |

*expressed in % w/w

The compositions of Table 3 were prepared as follows: HPLC grade water (50.0 parts) was added to vessel. The polymer (Potassium Acrylates Copolymer or Acrylates Copolymer), if present, was added to the water with mixing. The pH of each resulting solution was then adjusted with a 20% Sodium Hydroxide solution (as needed) until a final pH of about 6.8 was obtained. The remainder of the water was then added thereto.

The compositions of Table 3 were tested for Critical Micelle Concentration (CMC) values using the Equilibrium Tensiometry test with the surfactant Sodium Trideceth Sulfate (TDES). The Delta CMCs for each composition were calculated based on the CMC for comparable composition without any HMP (i.e. water) and such values are shown in Table 4 as an illustration of the efficiency of the polymers to associate surfactant thereto (and reduce irritation).

TABLE 4

| Equilibrium Tensiometry test results of HMP solution: | | | | |
|---|---|---|---|---|
| Examples | Potassium Acrylates Copolymer (mg/L) | CMC TDES (mg/L) | ΔCMC TDES (mg/L) | Efficiency ΔCMC/hmp |
| C7 | 0 | 136 | Na | na |
| C8 | 100 | 269 | 133 | 1.3 |
| C9 | 250 | 362 | 226 | 0.9 |
| C10 | 350 | 386 | 250 | 0.7 |
| C11 | 500 | 454 | 318 | 0.6 |
| C12 | 750 | 517 | 381 | 0.5 |
| Examples | Acrylates Copolymer (mg/L) | CMC TDES (mg/L) | ΔCMC TDES (mg/L) | Efficiency ΔCMC/hmp |
| C13 | 0 | 136 | Na | na |
| C14 | 100 | 291 | 155 | 1.6 |
| C15 | 250 | 410 | 274 | 1.1 |
| C16 | 375 | 468 | 332 | 0.9 |
| C17 | 500 | 431 | 295 | 0.6 |
| C18 | 750 | 434 | 298 | 0.4 |

The two HMP's, Potassium Acrylates Copolymer and Acrylates Copolymer, both exhibit an increase in the CMC, or a ΔCMC, suggesting an association of surfactant to the HMP. The efficiency of the association of surfactant to the HMP decreases with increasing HMP concentration. As more HMP is added to the surfactant system the mildness benefit is reduced. The association of surfactant to the Acrylates Copolymer plateaus at ~250 mg/L of polymer, and the association of surfactant to the Potassium Acrylates Copolymer plateaus at ~750 mg/L of polymer.

As stated above, the HMP, Acrylates Copolymer, approached a plateau of mildness improvement as measured by the TEP Test, at around 0.27% HMP. The HMP, Acrylates Copolymer, approached a plateau of mildness improvement as measured by the Equilibrium Tensiometry Test, at around 250 mg/L, or about 0.025% HMP. The TEP test is a dilution based test; the formulation is tested at between 0% to 15% and so the actives concentrations reported for the two tests vary by an order of magnitude. This is also done in order that both the TEP test and the Equilibrium Tensiometry Test evidence a plateau of the Acrylates Copolymer at the same concentration range.

As stated above, the HMP, Potassium Acrylates Copolymer, approached a plateau of mildness improvement as measured by the Equilibrium Tensiometry Test at around 750 mg/L, which is about 0.075% HMP. This is equivalent to 0.75% HMP in dilution based tests like TEP test and Skin Irritancy Potential Test.

Example 2

Comparatives C19-C22

Preparation of Cleansing Compositions: Polyglycerol-10 Laurate Mildness Dose Response The cleansing compositions of C19-C22 were prepared according to the procedure set forth in Example utilizing the materials and amounts listed in Table 5.

TABLE 5

| Cleansing Compositions with PG-10 Laurate | | | | |
|---|---|---|---|---|
| INCI name | C19 w/w % | C20 w/w % | C21 w/w % | C22 w/w % |
| Ammonium Lauryl Sulfate | 1.9 | 1.9 | 1.9 | 1.9 |
| Cocamidopropyl Betaine | 3.8 | 3.8 | 3.8 | 3.8 |
| Polyglycerol-10 | — | 0.5 | 2.0 | 6.0 |

TABLE 5-continued

Cleansing Compositions with PG-10 Laurate

| INCI name | C19 w/w % | C20 w/w % | C21 w/w % | C22 w/w % |
|---|---|---|---|---|
| Laurate | | | | |
| Glycerin | 0.5 | 0.5 | 0.5 | 0.5 |
| Fragrance | 0.2 | 0.2 | 0.2 | 0.2 |
| Potassium Sorbate | 0.5 | 0.5 | 0.5 | 0.5 |
| Sodium Hydroxide | qs | qs | qs | qs |
| Citric Acid | qs | qs | qs | qs |
| Deionized water | qs | qs | qs | qs |

*expressed in w/w % actives

Each of the compositions of Table 5 was independently prepared as follows: Water (50.0 parts) was added to a beaker. The following ingredients were then added thereto independently with mixing until each respective resulting mixture was homogenous: Polyglycerol-10 Laurate and the solution was heated to 70° C. After about 15 minutes of mixing, cooling was initiated. Then Ammonium Lauryl Sulfate, Cocamidopropyl Betaine, Potassium Sorbate, Glycerin and Fragrance as called for were added. The pH of the resulting solution was then adjusted with a 20% solution of Sodium Hydroxide or Citric Acid until the final desired pH of 6.0 was obtained. The remainder of the water was then added thereto.

TEP Test Mildness Comparison of Cleansing Compositions:

The compositions prepared in accordance with Comparatives C19-C22 were then tested for mildness in accordance with the above TEP Test. Table 6 lists the TEP value of the composition of each Example:

TABLE 6

TEP Test Mildness Comparison

| | Polyglycerol ester concentration (w/w %) | TEP $EC_{50}$ (% dilution) |
|---|---|---|
| C19 | 0 | 2.4 |
| C20 | 0.5 | 3.0 |
| C21 | 2.0 | 3.0 |
| C22 | 6.0 | 3.3 |

The addition of Polyglycerol-10 Laurate to the surfactant system increases the TEP test result, C19 compared to C20, which indicated the surfactant system is rendered milder with the addition of Polyglycerol-10 Laurate. In Comparatives C20-C22, the concentration of Polyglycerol-10 Laurate is increased and TEP test results are not observed to increase proportionally with the increase in Polyglycerol-10 Laurate concentration.

The increase in the TEP test results undergoes a plateau with increasing concentrations of Polyglycerol-10 Laurate; there is a loss of efficiency of the Polyglycerol-10 Laurate to improve the mildness of the surfactant system at high Polyglycerol-10 Laurate concentrations.

In many surfactant based systems, there is a need to have mildness improvements greater than what is achieved with 0.5% PG-10 Laurate. This is not achieved by addition of higher concentrations of PG-10 Laurate. The Polyglycerol-10 Laurate approached a plateau of mildness improvement at around 0.5% PG-10 Laurate.

Example 3

Comparative Examples C23-C25, and Inventive Example E1

Preparation of Cleansing Compositions

The cleansing compositions of C23-C25 and E1 were prepared in accordance with the procedure set forth in Example 1 utilizing the materials and amounts listed in Table 7.

TABLE 7

Cleansing Compositions

| INCI name | C23 w/w % | C24 w/w % | C25 w/w % | E1 w/w % |
|---|---|---|---|---|
| Ammonium Lauryl Sulfate | 1.9 | 1.9 | 1.9 | 1.9 |
| Cocamidopropyl Betaine | 3.8 | 3.8 | 3.8 | 3.8 |
| Polyglycerol-10 Laurate | 0.0 | 0.5 | 0.0 | 1.0 |
| Potassium Acrylates Copolymer | 0.0 | 0.0 | 0.9 | 0.9 |
| Glycerin | 0.5 | 0.5 | 0.5 | 0.5 |
| Fragrance | 0.2 | 0.2 | 0.2 | 0.2 |
| Potassium Sorbate | 0.5 | 0.5 | 0.5 | 0.5 |
| Sodium Hydroxide | Qs | qs | qs | qs |
| Citric Acid | Qs | Qs | qs | qs |
| Deionized water | Qs | Qs | qs | qs |

*expressed in w/w % actives

The $EC_{50}$ was measured for Comparatives C23-C25 and Inventive E1 using the TEP test. The $EC_H$ value for C23, the placebo with no Potassium Acrylates Copolymer and no Polyglycerol-10 Laurate, was subtracted from the $EC_{50}$ values for C24-C25 and E1. The differences are shown in FIG. 1.

In FIG. 1, the addition of 0.5% PG-10 Laurate increases the $EC_H$ in the TEP test (C24), compared to the placebo, and the addition of 0.9% Potassium Acrylates Copolymer increases the $EC_{50}$ in the TEP test (C25), compared to the placebo. From Examples 1 and 2, it is known that at concentrations of PG-10 Laurate or Potassium Acrylates Copolymer above 0.5% and 0.9%, respectively, the mildness does not increase proportionally to the concentration increase. Surprisingly, combining PG-10 Laurate and Potassium Acrylates Copolymer at 1.0% and 0.9%, respectively, provides a further increase in $EC_{50}$ in the TEP test (E1). This increase in mildness is achieved when both components are at concentrations greater than or about the level where efficiency is lost when used alone.

Example 4

Comparative Examples C26-C29 and Inventive Examples E2-E5

Preparation of Cleansing Compositions: Mildness with Combination of PG-10 Laurate and Potassium Acrylates Copolymer in Multiple Surfactant Systems The cleansing compositions of C26-C29 and E2-E5 were prepared according to the materials and amounts listed in Table 8. Also shown in Table 8 are the results of the Skin Irritancy Potential Test for each formulation.

TABLE 8

Cleansing compositions and Skin Irritancy Potential Test results (Concentration of IL-1α)

| INCI name | C26 w/w % | E2 w/w % | C27 w/w % | E3 w/w % | C28 w/w % | E4 w/w % | C29 w/w % | E5 w/w % |
|---|---|---|---|---|---|---|---|---|
| Ammonium Lauryl Sulfate | 1.5 | 1.2 | — | — | — | — | — | — |
| Sodium Isotridecyl Alcohol Sulfate | — | — | 2.8 | 2.8 | — | — | — | — |
| Sodium C14-16 Olefin Sulfonate | — | — | — | — | 2.0 | 2.0 | — | — |
| Cocamidopropyl Betaine | 3.0 | — | 2.5 | 2.5 | 3.6 | 3.6 | — | — |
| Cocamidopropyl Hydroxysultaine | 1.5 | 7.0 | — | — | — | — | 6.4 | 6.4 |
| Disodium lauroamphodiacetate | — | — | — | — | — | — | 4.4 | 4.6 |
| Polyglyceryl-10 Laurate | — | 1.9 | — | 1.9 | — | 1.5 | — | 1.0 |
| Potassium Acrylate Copolymer | 0.3 | 0.3 | 0.3 | 0.3 | 0.3 | 0.3 | 0.3 | 0.3 |
| Acrylates/C10-30 Alkyl Acrylate Crosspolymer | — | — | — | — | 0.3 | 0.3 | — | — |
| Glycerin | 0.5 | 0.5 | 0.5 | 0.5 | 0.5 | 0.5 | 0.5 | 0.5 |
| Fragrance | 0.2 | 0.2 | 0.2 | 0.2 | 0.2 | 0.2 | 0.2 | 0.2 |
| Phenoxyethanol; Ethylhexylglycerin | — | — | 0.8 | 0.8 | — | — | — | — |
| Potassium Sorbate | 0.5 | 0.5 | — | — | — | — | 0.5 | 0.5 |
| Sodium Benzoate | — | — | — | — | 0.5 | 0.5 | — | — |
| Sodium Chloride | — | — | — | — | 0.5 | — | — | — |
| Sodium Hydroxide | qs | qs | qs | qs | qs | qs | qs | qs |
| Citric Acid | qs | qs | qs | qs | qs | qs | qs | qs |
| Deionized water | qs | qs | qs | qs | qs | qs | qs | qs |
| IL-1α concentration (pg/mL) | 92.6 | 47.8 | 885.5 | 658.9 | 187.3 | 103.0 | 156.0 | 152.3 |

*expressed in w/w % actives

Each of the compositions of Table 8 was independently prepared as follows: Water (50.0 parts) was added to a beaker. The following ingredients were then added thereto independently with mixing until each respective resulting mixture was homogenous: Acrylates/C10-30 Alkyl Acrylate Crosspolymer as called for and the pH was adjusted to about 7.0 using a 20% Sodium Hydroxide solution. Then Polyglycerol-10 Laurate as called for and the solution was heated to 70° C. After about 15 minutes of mixing, cooling was initiated. Then Ammonium Lauryl Sulfate or Sodium Isotridecyl Alcohol Sulfate or Sodium C14-16 Olefin Sulfonate, and Cocamidopropyl Betaine or Cocamidopropyl Hydroxysultaine or Disodium Lauroamphodiacetate as called for were added. Then the hm-polymer Potassium Acrylates Copolymer (Lubrizol, Brecksville, Ohio) and the pH was adjusted to about 7.0 using a 20% Sodium Hydroxide solution. Then Potassium Sorbate or Sodium Benzoate or Phenoxyethanol and Ethylhexylglycerin, Glycerin, Sodium Chloride, and Fragrance as called for were added. The pH of the resulting solution was then adjusted with a 20% solution of Sodium Hydroxide or Citric Acid until the final desired pH of 4.8 (Sodium Benzoate), 6.0 (Potassium Sorbate), or 7.0 (Phenoxyethanol and Ethylhexylglycerin) was obtained. The remainder of the water was then added thereto.

Also shown in Table 8 are the results of the Skin Irritancy Potential Test for each formulation. All formulations in Table 8, Comparative examples and Inventive examples, contain 0.3% Potassium Acrylates Copolymer. The absolute value of the IL-1α concentration differs dependent on the base surfactant system. The concentration of IL-1α decreases with addition of PG-10 Laurate for all surfactant systems that contain at least one anionic surfactant, indicating a further increase in mildness with the addition of PG-10 Laurate and combination with Potassium Acrylates Copolymer (E2-E4). The impact of PG-10 Laurate on formulation mildness is less when the surfactant base is traditionally milder, such as some blends of amphoteric surfactants (E5).

Example 5

Inventive Examples E6-E7

Preparation of Cleansing Compositions: Mildness with Combination of PG-10 Laurate and Potassium Acrylates Copolymer at High Concentration The cleansing compositions of E6-E7 were prepared in accordance with the procedure set forth in Example 1 utilizing the materials and amounts listed in Table 9. Also shown in Table 9 are the results of the Skin Irritancy Potential Test for each formulation.

TABLE 9

Cleansing compositions and Skin Irritancy Potential Test results (Concentration of IL-1α)

| INCI name | E6 w/w % | E7 w/w % |
|---|---|---|
| Coco-Betaine | 3.0 | 3.6 |
| Disodium Lauroamphodiacetate | 3.7 | 3.0 |
| Polyglyceryl-10 Laurate | 0.5 | 6.0 |
| Potassium Acrylate Copolymer | 0.3 | 0.9 |
| Glycerin | 0.5 | 0.5 |
| Fragrance | 0.2 | 0.2 |
| Potassium Sorbate | 0.5 | 0.5 |
| Sodium Hydroxide | qs | qs |
| Citric Acid | qs | qs |
| Deionized water | qs | Qs |
| IL-1α concentration (pg/mL) | 366.2 | 74.0 |

*expressed in w/w % actives

Each of the compositions of Table 9 was independently prepared as follows: Water (50.0 parts) was added to a beaker. The following ingredients were then added thereto independently with mixing until each respective resulting mixture was homogenous: Polyglycerol-10 Laurate and the solution was heated to 70° C. Then Coco-betaine, Disodium Lauroamphodiacetate, the hm-polymer Potassium Acrylates Copolymer (Lubrizol, Brecksville, Ohio) and the pH was adjusted to about pH 7.0 using a 20% Sodium Hydroxide solution, then Potassium Sorbate, Glycerin and Fragrance as called for were added. The pH of the resulting solution was then adjusted with a 20% solution of Sodium Hydroxide or Citric Acid until the final desired pH of 6.0 was obtained. The remainder of the water was then added thereto.

Also shown in Table 9 are the results of the Skin Irritancy Potential Test for each formulation. All formulations in Table 9 include Potassium Acrylates Copolymer and Polyglycerol-10 Laurate at concentrations similar to those shown above in Table 8. Example E7 contains both Potassium Acrylates Copolymer and Polyglycerol-10 Laurate at concentrations much greater than Example E6. As stated above, increasing concentration of Potassium Acrylates Copolymer above the plateau concentration of about 0.75% does not provide a proportional increase in mildness. As stated above, increasing the concentration of Polyglycerol-10 Laurate above the plateau concentration of about 0.5% does not provide a proportional increase in mildness. As stated above, combining PG-10 Laurate and Potassium Acrylates Copolymer provides an increase in mildness. Surprisingly, combining PG-10 Laurate and Potassium Acrylates Copolymer at concentrations much higher than their plateau concentrations provides a substantial increase in mildness as measured by the Skin Irritancy Potential Test (E7).

Example 6

Comparative example C30 and Inventive examples E6-E9

Preparation of Cleansing Compositions: Potassium Acrylates Copolymer and PGEs

The cleansing compositions of C33-C34 and E8-E12 were prepared according to the procedure set forth in Example 1 utilizing the materials and amounts listed in Table 10.

TABLE 10

Cleansing Compositions with HMP and PGE's

| INCI name | C30 w/w % | E8 w/w % | E9 w/w % | E10 w/w % | E11 w/s % | E12 w/w % |
|---|---|---|---|---|---|---|
| Sodium C14-16 Olefin Sulfonate | 2.2 | 2.2 | 2.2 | 2.2 | 2.2 | 2.2 |
| Cocamidopropyl Betaine | 3.0 | 3.0 | 3.0 | 3.0 | 3.0 | 3.0 |
| Polyglycerol-10-Laurate | — | 3.0 | — | — | — | — |
| Polyglycerol-10-Myristate | — | — | 3.0 | — | — | — |
| Polyglycerol-10-Oleate | — | — | — | 0.75 | 1.5 | 3.0 |
| Potassium Acrylates Copolymer | 1.0 | 1.0 | 1.0 | 1.0 | 1.0 | 1.0 |
| Glycerin | 0.5 | 0.5 | 0.5 | 0.5 | 0.5 | 0.5 |
| Sodium Benzoate | 0.5 | 0.5 | 0.5 | 0.5 | 0.5 | 0.5 |
| Sodium Hydroxide | qs | qs | qs | qs | qs | qs |
| Water | qs | qs | qs | qs | qs | qs |

*expressed in % w/w

Each of the compositions of Table 10 was independently prepared as follows: Water (50.0 parts) was added to a beaker. For examples C30 and E8-E12, Potassium Acrylates Copolymer was added to the water with mixing. The PGE (either Polyglycerol-10-Laurate, Polyglycerol-10-Myrlstate, or Polyglycerol-10-Oleate) was then added thereto with mixing, and the following ingredients were then added thereto independently with mixing until each respective resulting mixture was homogenous: Cocamidopropyl Betaine, Sodium C14-16 Olefin Sulfonate, Glycerin, and Sodium Benzoate. The pH of the resulting solution was then adjusted with a 20% Sodium Hydroxide or Citric Acid solution until a final pH of about 4.8 was obtained. The remainder of the water was then added thereto.

Foam Volume Test of Cleansing Compositions: The compositions prepared in accordance with Comparative C30 and Inventive Examples E8-E12 were then tested for foaming generation in accordance with the above Foam Volume Test Table 11 lists the Foam Volume results of the composition of each Example.

TABLE 11

Foam Volume Test

| | C30 | E9 | E10 | E11 | E12 |
|---|---|---|---|---|---|
| Foam Test results (900 RPM) | | | | | |
| PGE | — | PG-10-M (3.0%) | PG-10-O (0.75%) | PG-10-O (1.5%) | PG-10-O (3.0%) |
| Foam Vol (ml @ 30 s) | 95 | 134 | 138 | 122 | 133 |
| Foam Vol (ml @ 160 s) | 168 | 175 | 174 | 171 | 177 |
| Foam Test results (1200 RPM) | | | | | |
| PGE | — | PG-10-M (3.0%) | PG-10-O (0.75%) | PG-10-O (1.5%) | PG-10-O (3.0%) |
| Foam Vol (ml @ 30 s) | 113 | 195 | 208 | 147 | 172 |
| Foam Vol (ml @ 160 s) | 286 | 506 | 628 | 393 | 497 |

The addition of different PGE surfactants, PG-10-L, PG-10-M, PG-10-O, all add to the foam of the surfactant system at both rpm's investigated.

Skin Irritancy Potential Test Results of Cleansing Compositions: The compositions prepared in accordance with Comparative C30 and Inventives E8, E9, E11, and E12 were then tested for their irritancy potential in accordance with the above Skin Irritancy Potential Test: Table 12 lists the Skin Irritancy Potential Test results of the composition of each Example:

TABLE 12

Skin Irritancy Potential Results of Cleansing Composition with HMP and PGE's

| | C30 | E8 | E9 | E11 | E12 |
|---|---|---|---|---|---|
| PGE | — | PG-10-L (3.0%) | PG-10-M (3.0%) | PG-10-O (1.5%) | PG-10-O (3.0%) |
| Il-1a (pg/mL) | 236 | 150.0 | 119.4 | 94.3 | 74.3 |

The addition of different PGE surfactants, PG-10-L, PG-10-M, PG-10-O, all improve the mildness of the surfactant system. Surprisingly even though the PGE surfactants improve the mildness of the surfactant system, the PGE's also improve the foam of the cleanser. Generally increased foaming is correlated with harsher, less mild, surfactant systems.

What is claimed is:

1. A skin cleansing composition comprising:
   (a) a low molecular weight, non-crosslinked, hydrophobically modified linear acrylic copolymer wherein the low molecular weight copolymer has a number average molecular weight of about 100,000 or less;
   (b) an ester of a fatty acid and a glycerin polymer, wherein said ester has x glycerin repeat units and a carbon chain length of n,
   wherein x is from 8 to 14; and n is from 10 to 18;
   (c) at least one surfactant selected from the group consisting of an anionic surfactant or an amphoteric or a mixture thereof wherein said surfactants are present in an amount of from about 2 to about 7 weight percent of said skin cleansing composition.

2. A skin cleansing composition according to claim 1 wherein said total surfactant load, including said anionic surfactant, said amphoteric surfactant and said ester of a fatty acid and a glycerin polymer having the formula PGE-x-n of said skin cleansing composition is not greater than about 15 weight percent of the skin cleansing composition.

3. A skin cleansing composition according to claim 1 wherein the ratio of x:n is from about 1 to about 2.

4. A skin cleansing composition according to claim 1 wherein x is from about 10 to about 12.

5. A skin cleansing composition according to claim 1 wherein x is 10.

6. A skin cleansing composition according to claim 1 wherein n is from about 12 to about 18.

7. A skin cleansing composition according to claim 1 wherein n is from about 12 to about 16.

8. A skin cleansing composition according to claim 1 wherein said anionic surfactant is selected from the group consisting of alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, and mixtures of two or more thereof.

9. A skin cleansing composition according to claim 1 wherein said ester of a fatty acid and glycerin polymer is selected from the group consisting of Polyglyceryl-8 Caprylate/Caprate, Polyglyceryl-8 Laurate, Polyglyceryl-9 Laurate, Polyglyceryl-10 Laurate, Polyglyceryl-8 Cocoate, Polyglyceryl-9 Cocoate, Polyglyceryl-10 Cocoate, Polyglyceryl-11 Cocoate, Polyglyceryl-12 Cocoate, Polyglyceryl-8 Myristate, Polyglyceryl-9 Myristate, Polyglyceryl-10 Myristate, Polyglyceryl-11 Myristate, Polyglyceryl-12 Myristate, Polyglyceryl-8 Palmitate, Polyglyceryl-9 Palmitate, Polyglyceryl-10 Palmitate, Polyglyceryl-11 Palmitate, Polyglyceryl-12 Palmitate, Polyglyceryl-10 Oleate, Polyglyceryl-11 Oleate, Polyglyceryl-12 Oleate, Polyglyceryl-10 Stearate, Polyglyceryl-12 Stearate, Polyglyceryl-14 Stearate and Polyglyceryl-14 Oleate and combinations of two or more thereof.

10. A skin cleansing composition according to claim 1 wherein said amphoteric surfactant is selected from the group consisting of amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

11. A skin cleansing composition according to claim 2 wherein said compositions comprise from about 2 to about 7 weight percent total surfactant.

12. A skin cleansing composition according to claim 11 wherein said compositions comprise from about 1.5 to about 5 weight percent total surfactant.

13. A skin cleansing composition according to claim 1 wherein said composition exhibits a foam volume greater than about 100 ml at 30 s with 900 rpm.

14. A skin cleansing composition according to claim 1 wherein said composition exhibits a foam volume greater than about 160 ml at 160 s with 900 rpm.

* * * * *